United States Patent [19]

Merkle et al.

[11] 4,097,521

[45] Jun. 27, 1978

[54] MANUFACTURE OF AMIDOSULFONIC ACIDS

[75] Inventors: Hans Rupert Merkle, Ludwigshafen; Albrecht Müeller, Frankenthal, both of Germany

[73] Assignee: BASF Aktiengesellschaft, Ludwigshafen, Germany

[21] Appl. No.: 796,548

[22] Filed: May 13, 1977

[30] Foreign Application Priority Data

Jun. 23, 1976 Germany .............................. 2628195

[51] Int. Cl.$^2$ ......................................... C07C 143/86
[52] U.S. Cl. ............................ 260/513.6; 260/543 R; 260/566 R
[58] Field of Search ...................................... 260/513.6

[56] References Cited

U.S. PATENT DOCUMENTS

| 2,102,350 | 12/1937 | Baumgarten | 260/513.6 |
| 2,662,094 | 12/1953 | Kamlet | 260/513.6 |
| 2,689,174 | 9/1954 | Kamlet | 260/513.6 |
| 3,555,081 | 1/1971 | Zirner et al. | 260/513.6 |

FOREIGN PATENT DOCUMENTS

| 1,156,402 | 10/1963 | Germany | 260/513.6 |
| 39-19440 | 9/1964 | Japan | 260/513.6 |
| 584,914 | 1/1947 | United Kingdom | 260/513.6 |

*Primary Examiner*—Joseph E. Evans
*Attorney, Agent, or Firm*—Keil, Thompson & Shurtleff

[57] ABSTRACT

Amidosulfonic acids are manufactured by reacting Schiff bases first with sulfur trioxide and then with water. The compounds obtainable by the process of the invention are sweeteners (especially in the case of cyclohexylamidosulfonic acid and its calcium, sodium and potassium salts), and valuable starting materials for the manufacture of sweeteners, dyes and pesticides.

7 Claims, No Drawings

MANUFACTURE OF AMIDOSULFONIC ACIDS

The present invention relates to a new process for the manufacture of amidosulfonic acids by reacting Schiff bases first with sulfur trioxide and then with water.

Houben-Weyl, Methoden der Organischen Chemie, Volume 11/2, pages 654–655, discloses than N,N'-dialkylureas can, by the action of oleum, be first sulfonated and then split to give amidosulfonic acids. A publication in J.Amer. Chem.Soc., 75 (1953), 1,408 also deals with the reaction with oleum, described by Houben-Weyl, without further after-treatment; it expressly draws attention to the difficulty of achieving optimum yield from the reaction and in particular of suppressing or reducing the formation of alkylammonium sulfate. The time at which the starting materials are added, and the temperature control of the reaction, play an important part. On working up, the end product must be washed repeatedly with ether but in spite of these purification treatments it still contains sulfate and can only be finally purified by dissolving it in methanol and precipitating it by adding substantial amounts of ether. U.S. Pat. No. 3,555,081 describes the synthesis of N-cyclohexylamidosulfonic acid and also shows that the use of sulfuric acid leads to contaminated end products. According to this disclosure (column 3, lines 45–54), the absence of sulfuric acid from the reaction mixture is critical. In two-stage methods, sulfuric acid must only be used together with sulfur trioxide, in the form of oleum, in the second reaction stage.

German Laid-Open Application DOS 2,164,197 discloses the reaction of isocyanates with sulfuric acid in organic solvents, at elevated temperatures, to give amidosulfonic acids. This process is unsatisfactory because the starting materials are toxic and in some cases difficult to obtain, the reaction is difficult to carry out and the yield is only moderate.

We have found that amidosulfonic acids of the formula

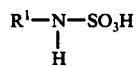

where $R^2$ is an aliphatic or cycloaliphatic radical, are obtained in an advantageous manner when Schiff bases of the formula

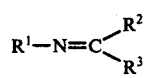

where $R^1$ has the above meaning and $R^2$ and $R^3$ may be identical or different and each is an aliphatic or cycloaliphatic radical or a furyl radical, and $R^2$ may also be hydrogen, are reacted with sulfur trioxide in a first step and the adduct formed is reacted with water in a second step.

Where ethylidene-isopropylamine is used, the reaction may be represented by the following equations:

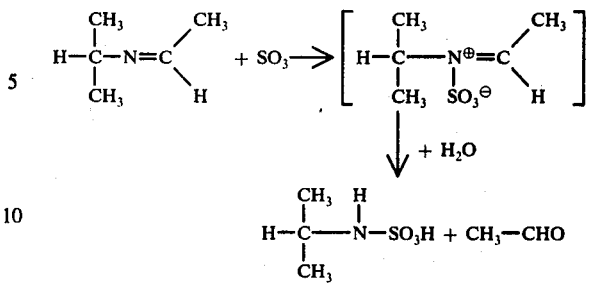

Compared to the conventional process, the process of the invention starts from more readily obtainable raw materials and, surprisingly, gives amidosulfonic acids more simply and more economically, and in good yield and high purity. Since the ketones and aldehydes recovered from the reaction can be reconverted to the Schiff bases by reaction with the amines, the process of the invention provides a means of manufacturing amidosulfonic acids from amines and $SO_3$, via Schiff bases. Compared to the processes using isocyanates as starting materials, the new process furthermore causes less environmental pollution and is more reliable in operation.

Preferred starting materials II and, accordingly, preferred end products I are those where $R^1$ is alkyl of 1 to 20, preferably 1 to 10, carbon atoms or cycloalkyl of 4 to 8 carbon atoms, $R^2$ and $R^3$ are identical or different and each is alkyl of 1 to 20, preferably 1 to 10, carbon atoms or cycloalkyl of 4 to 8 carbon atoms or furyl, and $R^2$ may also be hydrogen. The above radicals may furthermore be substituted by groups which are inert under the reaction conditions, eg. alkyl of 1 to 4 carbon atoms.

The following are examples of Schiff bases suitable as starting materials II: the methyl-, ethyl-, n-propyl-, isopropyl-, n-butyl-, isobutyl-, sec.-butyl-, tert.-butyl-, n-pentyl-, pentyl-2-, pentyl-3-, n-hexyl-, n-heptyl-, n-octyl-, n-nonyl-, n-decyl-, 2-ethylhexyl-, 2,2,6-trimethyl-n-heptyl-, 2-ethylpentyl-, 3-ethylpentyl-, 2,3-dimethyl-n-butyl-, 2,2-dimethyl-n-butyl-, 2-methylpentyl-, 3-methylpentyl-, cyclobutyl-, cyclopentyl-, cyclohexyl-, cycloheptyl- and cyclooctyl-imine of acetaldehyde, propionaldehyde, n-butyraldehyde, iso-butyraldehyde, 2-methyl-butyraldehyde, 2-ethyl-capronaldehyde, n-valeraldehyde, isovaleraldehyde, 2,2-dimethyl-propionaldehyde, n-capronaldehyde, isocapronaldehyde, 2-methyl-valeraldehyde, 3-methyl-valeraldehyde, 2-ethyl-butyraldehyde, 2,2-dimethylbutyraldehyde, 2,3-dimethylbutyraldehyde, 3,3-dimethylbutyraldehyde, enanthaldehyde, 2-methyl-capronaldehyde, 3-methyl-capronaldehyde, 4-methyl-capronaldehyde, 5-methyl-capronaldehyde, 2-ethyl-valeraldehyde, 2,2-dimethyl-valeraldehyde, 3-ethylvaleraldehyde, 3,3-dimethyl-valeraldehyde, 2,3-dimethylvaleraldehyde, 4-ethyl-valeraldehyde, 4,4-dimethylvaleraldehyde, 3,4-dimethylvaleraldehyde, 2,4-dimethylvaleraldehyde, 2-ethyl-2-methyl-butyraldehyde, 2-ethyl-3-methyl-butyraldehyde, acetone, methyl ethyl ketone, methyl n-propyl ketone, methyl isopropyl ketone, methyl n-butyl ketone, methyl isobutyl ketone, methyl sec.-butyl ketone, methyl tert.-butyl ketone, methyl n-pentyl ketone, methyl pentyl-2 ketone, methyl pentyl-3 ketone, methyl isoamyl ketone, methyl (2-methyl)-butyl ketone, methyl (1-methyl)-butyl ketone, methyl (2-ethyl)-butyl ketone, methyl (3-ethyl)-butyl ketone, methyl (2,2-dimethyl)- butyl ketone, methyl (2,3)-dimethyl)-butyl ketone and methyl (3,3-dimethyl)-butyl ketone, corresponding unsymmetrical ketones, which instead of the methyl group carry the ethyl, n-propyl, isopropyl, n-butyl, isobutyl, sec.-butyl, tert.-butyl, n-pentyl, pentyl-2, pentyl-3, isoamyl, (2-methyl)-butyl, (1-methyl)-butyl, (2-ethyl)-butyl, (3-ethyl)-butyl, (2,2-dimethyl)-butyl, (2,3-dimethyl)-butyl and (3,3-dimethyl)-butyl group, diethyl ketone, di-n-propyl ketone, di-iso-propyl ketone, di-n-butyl ketone, di-iso-butyl ketone, di-sec.-butyl ketone, di-tert.-butyl ketone, di-n-pentyl ketone, dipentyl-2 ketone, dipentyl-3 ketone, diisoamyl ketone, di-(2-methyl)-butyl ketone, di-(1-methyl)-butyl ketone, di-(2-ethyl)-butyl ketone, di-(3-ethyl)-butyl ketone, di-(2,2-dimethyl)-butyl ketone, di-(2,3-dimethyl)-butyl ketone, di-(3,3-dimethyl-butyl ketone, cyclohexylaldehyde and cyclopentylaldehyde, dicyclopentyl ketone and dicyclohexyl ketone, and furfuraldehyde; the Schiff bases listed in the Examples are preferred.

The reaction is advantageously carried out with from 0.8 to 1.5, preferably from 0.95 to 1.1, moles of sulfur trioxide per mole of starting material II in the first step and with from 0.9 to 10, especially from 1 to 10, preferably from 1 to 2, moles of water per mole of starting material II in the second step. The sulfur trioxide may be employed in the solid form or, advantageously in the liquid form or as a gas; the use of 100 percent strength sulfur trioxide is advantageous, though the material may also be diluted with an inert gas such as carbon dioxide. However, it is also possible to use compounds which release sulfur trioxide under the reaction conditions, for example adducts of sulfur trioxide, eg. with ethers such as tetrahydrofuran, di-($\beta$-chloroethyl) ether or 1,4-dioxane, with N,N-disubstituted carboxylic acid amides, eg. N,N-dimethylformamide, and with tertiary amines, eg. pyridine, triethylamine, trimethylamine, tributylamine, quinoline, quinaldine, dimethylaniline, triphenylamine, N-methylmorpholine, N-ethylmorpholine, N-methylpiperidine, N-ethylimidazole, N-methylethyleneimine and N-ethylpentamethyleneimine, or adducts of chlorosulfonic acid with the above amines, especially with pyridine, or corresponding mixtures. Compounds which contain sulfuric acid, eg. oleum, cannot be used in place of sulfur trioxide. With regard to the definition of 100 percent strength sulfur trioxide, reference may be made to Ullmanns Encyklopadie der technischen Chemie, Volume 15, pages 465–467, whilst with regard to the manufacture of adducts reference may be made to Houben-Weyl, (loc. cit.), Volume VI/2, pages 455–457 and Volume IX, pages 503–508.

The two-stage reaction is in general carried out at from $-30°$ C to $+150°$ C, the first stage advantageously being carried out at from $-30°$ to $+100°$ C, preferably from $-20°$ to $+30°$ C, and the second stage advantageously at from $-20°$ to $+150°$ C, preferably from $-10°$ to $+100°$ C; the reaction may be carried out under atmospheric pressure or superatmospheric pressure, continuously or batchwise. Advantageously, organic solvents which are inert under the reaction conditions are used in both stages though it is advantageous if the total amount of organic solvent is added already in the first reaction step. Examples of suitable solvents are halohydrocarbons, especially chlorohydrocarbons, eg. tetrachloroethylene, amyl chloride, cyclohexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, tetrachloroethane, trichloroethane, trichloroethylene, pentachloroethane, trichlorofluoromethane, cis-dichloroethylene, o-, m- and p-difluorobenzene, 1,2-dichloroethane, 1,1-dichloroethane, n-propyl chloride, 1,2-cis-dichloroethylene, n-butyl chloride, 2-, 3- and isobutyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane, aliphatic or cycloaliphatic hydrocarbons, eg. heptane, pinane, nonane, gasoline fractions with boiling ranges or from 70° to 190° C, cyclohexane, methylcyclohexane, petroleum ether, decalin, pentane, hexane, naphtha, 2,2,4-trimethylpentane, 2,2,3-trimethylpentane, 2,3,3-trimethylpentane and octane, and corresponding mixtures. The solvent is advantageously used in an amount of from 100 to 10,000 percent by weight, preferably from 100 to 1,000 percent by weight, based on starting material I.

After the first stage, the adduct can be isolated from the reaction mixture, for example by filtration, or by removing the solvent, and can then be returned to the second stage. In general, however, if only for economic and operational reasons, the two stages of the reaction are carried out successively without isolating the adduct, and accordingly the reaction mixture from the first stage is treated directly with water.

The reaction may be carried out as follows: a mixture of starting material II, with or without organic solvent, and sulfur trioxide is kept at the reaction temperature for from 0.2 to 3 hours. It is advantageous first to add the sulfur trioxide to a solvent and then to add the starting material II, with thorough mixing. Water is then added and in the second reaction stage the mixture is kept at the reaction temperature for from 0.5 to 2 hours. The end product is then isolated from the reaction mixture in the conventional manner, for example by filtration.

The compounds which may be manufactured by the process of the invention are sweeteners (especially in the case of cyclohexylamidosulfonic acid and its calcium, sodium and potassium salts) and valuable starting materials for the manufacture of sweeteners, dyes and pesticides. For example, the corresponding sulfonic acid chlorides, eg. isopropylaminosulfonyl chloride, can be manufactured by chlorination, eg. with thionyl chloride, and from these the o-sulfamidobenzoic acids described in German Laid-Open Application DOS 2,104,682 can be manufactured by reaction with anthranilic acid or its salts. Cyclizing the o-sulfamidobenzoic acids, eg. by the process described in German Laid-Open Application DOS 2,105,687, gives the 2,1,3-benzothiadiazin-4-one-2,2-dioxides, the use of which as crop protection agents and drugs is described in the same patent. Regarding the use of the amidosulfonic acids, reference may be made to the above publication and to German Published Application DAS 1,120,456, German Patent 1,242,627 and German Laid-Open Application DOS 1,542,836.

In the Examples which follow, parts are by weight.

EXAMPLE 1

80 parts of $SO_3$ are dissolved in 120 parts of dichloroethane and the solution is cooled to $-20°$ C. 113 parts of isobutylideneisopropylamine in 100 parts of dichloroethane are added in the course of 20 minutes; the temperature slowly rises to 0° C. The mixture is stirred for one hour and 18 parts of water are then added in the course of 10 minutes, at 0° C. After again stirring for 1 hour, the mixture is filtered and after drying, 136 parts (98.5% of theory) of isopropylamidosulfonic acid of melting point 171° C are obtained. Isobutyraldehyde was isolated from the filtrate by distillation and converted to the Schiff base by reaction with fresh isopropylamine.

EXAMPLE 2

80 parts of SO₃ are introduced into 100 parts od dichloroethane at −10° C. At this temperature, 99 parts of isopropylideneisopropylamine in 100 parts of dichloroethane are added in the course of 30 minutes. 18 parts of water are then added in the course of 10 minutes at 10° C. The end product formed is now filtered off and after drying, 131 parts (95% of theory) of isopropylamidosulfonic acid of melting point 170° C are obtained.

EXAMPLE 3

101 parts of the Schiff base from pivalinaldehyde and isopropylamine in 100 parts of chloroform are added to 80 parts of SO₃ in 100 parts of chloroform in the course of 30 minutes, at 0° C. Following the method described in Example 1, 120 parts (87% of theory) of isopropylamidosulfonic acid are obtained.

EXAMPLE 4

20.4 parts of ethylidene-isopropylamine are added to 19.25 parts of SO₃ in 50 parts of dichloroethane in the course of 15 minutes at −10° C. After stirring for one hour, the mixture is treated with 4.5 parts of water at 5° C. After filtering and drying, 28.3 parts (85.5% of theory) of isopropylamidosulfonic acid of melting point 170° C are obtained.

EXAMPLE 5

45.4 parts of isobutylidene-cyclohexylamine are added in the course of 30 minutes to 19.25 parts of SO₃ in 100 parts of dichloroethane at −10° C. The mixture is then stirred for 1 hour at 0° C, after which it is treated with 4.5 parts of water in the course of 5 minutes at 0° C. The resulting suspension is filtered after stirring for 1.5 hours, and the mother liquor is evaporated under 40 mbar pressure. The residue is combined with the material on the filter, and dried. 42.0 parts of cyclohexylamidosulfonic acid (97.5% of theory) of melting point 169° C are obtained.

EXAMPLE 6

32.8 parts of furfurylidene-isopropylamine are added to 19.25 parts of SO₃ in 100 parts of dichloroethane in the course of 15 minutes at −10° C. At the start of the addition, the reaction solution becomes reddish violet, whilst towards the end of the addition the color again lightens. The mixture is stirred for a further 1.5 hours at −10° C, and 4.5 parts of water are then added at the same temperature. The yellow precipitate which forms after 30 minutes is filtered off and dried. 23.6 parts (78% of theory) of isopropylamidosulfonic acid of melting point 167° C are obtained.

EXAMPLE 7

64.5 parts of isobutylidene-dodecylamine in 100 parts of dichloroethane are added to 21.5 parts of SO₃ in 150 parts of 1,2-dichloroethane in the course of 15 minutes at −10° C. The solution is heated to 0° C in the course of 1 hour, and 4.9 parts of water are added rapidly.

After a further 15 minutes, a finely crystalline precipitate forms. After filtration and drying, 65 parts of dodecylamidosulfonic acid of melting point 160° C (with decomposition) are obtained.

EXAMPLE 8

(a) 31 parts of SO₃ are introduced into 70 parts of CCl₄. 43.8 parts of isobutylidene-isopropylamine in 100 parts of CCl₄ are now added at −10° C in the course of 40 minutes. After completion of the addition, the mixture is filtered and th filter residue is dried. It consists of 74.5 parts of the adduct of the formula $$\left[\begin{array}{c} CH_3 \\ | \\ HC-\!\!-\!\!N^{\oplus}\!\!=\!\!C-\!\!C \\ | \quad | \\ CH_3 \quad SO_3^{\ominus} \end{array}\begin{array}{c} H \\ | \\ \\ \\ \end{array}\begin{array}{c} CH_3 \\ / \\ \\ \backslash \\ CH_3 \end{array}\right]$$

of melting point 72° C (with decomposition).

(b) 50 parts of the above adduct are suspended in 100 parts of chloroform at −10° C and 4.7 parts of water are added. The mixture is stirred at −10° C for 15 minutes and the product is filtered off and dried. 35 parts of isopropylamidosulfonic acid of melting point 171° C are obtained.

We claim:

1. A process for the manufacture of amidosulfonic acids of the formula

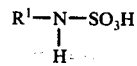

where R¹ is an aliphatic or cycloaliphatic radical, which comprises reacting a Schiff base of the formula

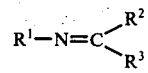

where R¹ has the above meanings and R² and R³ may be identical or different and each is an aliphatic or cycloaliphatic radical or a furyl radical, and R² may also be hydrogen, with sulfur trioxide in a first stage and then reacting the adduct formed in the first stage with water in a second stage.

2. A process as claimed in claim 1, wherein the reaction is carried out, in the first stage, with from 0.8 to 1.5 moles of sulfur trioxide per mole of starting material II.

3. A process as claimed in claim 1, wherein the reaction is carried out, in the second stage, with from 0.9 to 10 moles of water per mole of starting material III.

4. A process of as claimed in claim 1, wherein the reaction is carried out in both stages at from −30° to +150° C.

5. A process as claimed in claim 1, wherein the reaction is carried out, in the first stage, at from −30° to +100° C.

6. A process as claimed in claim 1, wherein the reaction is carried out, in the second stage, at from −20° to +150° C.

7. A process as claimed in claim 1, wherein the reaction is carried out, in both stages, in the presence of from 100 to 10,000 percent by weight, based on starting material I, of organic solvents which are inert under the reaction conditions.

* * * * *

UNITED STATES PATENT AND TRADEMARK OFFICE
CERTIFICATE OF CORRECTION

PATENT NO. : 4,097,521
DATED : June 27, 1978
INVENTOR(S) : MERKLE ET AL

It is certified that error appears in the above-identified patent and that said Letters Patent are hereby corrected as shown below:

In claim 3, line 3, cancel "III" and substitute --II--.

Signed and Sealed this

Eighth Day of May 1979

[SEAL]

Attest:

RUTH C. MASON
Attesting Officer

DONALD W. BANNER
Commissioner of Patents and Trademarks